United States Patent [19]

Ptchelintsev

[11] Patent Number: 5,972,993
[45] Date of Patent: Oct. 26, 1999

[54] COMPOSITION AND METHOD FOR TREATING ROSACEA AND SENSITIVE SKIN WITH FREE RADICAL SCAVENGERS

[75] Inventor: Dmitri Ptchelintsev, Mahwah, N.J.

[73] Assignee: Avon Products, Inc., New York, N.Y.

[21] Appl. No.: 09/045,087

[22] Filed: Mar. 20, 1998

[51] Int. Cl.$^6$ .............................. A61K 6/00; A61K 7/00
[52] U.S. Cl. ................ 514/449; 424/195.1; 424/401; 514/27; 514/32; 514/33; 514/281; 514/451; 514/453; 514/454; 514/456; 514/457; 514/458; 514/460; 514/474; 514/532; 514/549; 514/553; 514/560; 514/562; 514/568; 514/569; 514/570; 514/706; 514/712; 514/713; 514/715
[58] Field of Search .............................. 424/401, 195.1; 514/27, 32, 33, 281, 451, 449, 453, 454, 456, 457, 458, 460, 474, 532, 549, 553, 560, 562, 568, 569, 570, 706, 712, 713, 715, 717, 718, 762, 855, 887

[56] References Cited

U.S. PATENT DOCUMENTS

| 4,133,893 | 1/1979 | Spangler | 424/354 |
|---|---|---|---|
| 4,837,378 | 6/1989 | Borgman | 424/81 |
| 5,438,073 | 8/1995 | Saurat et al. | 514/452 |
| 5,569,651 | 10/1996 | Garrison et al. | 514/159 |

FOREIGN PATENT DOCUMENTS

| 0 722 722 A1 | 7/1996 | European Pat. Off. . |
|---|---|---|
| 0 722 928 A1 | 7/1996 | European Pat. Off. . |
| 0 734 729 A1 | 10/1996 | European Pat. Off. . |
| 0 737 471 A2 | 10/1996 | European Pat. Off. . |
| 0 756 862 A1 | 2/1997 | European Pat. Off. . |
| 2597337A2 | of 1987 | France . |
| 2728165A1 | of 1996 | France . |
| 3514724 A1 | 10/1986 | Germany . |
| 4123615 A1 | 2/1993 | Germany . |
| 1776411 A1 | 11/1992 | U.S.S.R. . |
| 1822781 A1 | 6/1993 | U.S.S.R. . |
| WO 88/00465 | 1/1988 | WIPO . |
| WO 88/06888 | 9/1988 | WIPO . |
| WO 93/20817 | 10/1993 | WIPO . |

OTHER PUBLICATIONS

Derwent Abstract for SU 1776411 A1.
Derwent Abstract for SU 1822781 A1.
De Rios et al., Journal Of Investigative Dermatology, 70 (3) 123–5 (Abstract), 1978.
English Translation of FR 2,597,337 (France) Published Oct. 23, 1987.

Primary Examiner—Frederick Krass
Attorney, Agent, or Firm—Ohlandt, Greeley, Ruggiero & Perle, LLP

[57] ABSTRACT

A method for treating skin conditions, such as rosacea and sensitive skin, that manifest as a tendency towards flushing and blushing is provided. Also provided herein, are compositions for the treatment of rosacea and sensitive skin that are comprised of at least one antioxidant selected from the following groups of antioxidants: (a) phenolic compounds that contain at least one hydroxyl group connected directly to a benzene ring and to another unsaturated chemical grouping, (b) sulfur-containing compounds that contain at least one sulfhydryl groups or sulfur-containing compounds that contain at least one disulfide group, or (c) polyene compounds that have conjugated systems of double bonds.

19 Claims, 2 Drawing Sheets

COMPOSITION AND METHOD FOR TREATING ROSACEA AND SENSITIVE SKIN WITH FREE RADICAL SCAVENGERS

BACKGROUND OF THE INVENTION

1. Field of the Invention

The present invention concerns a method and composition for treating skin disorders, such as rosacea and sensitive skin, with free radical scavengers, which are also known as antioxidants. More particularly, the present invention involves the treatment of rosacea by the topical application of a cosmetically acceptable formulation containing free radical scavenging compounds. The terms "radical scavenger(s)" and "antioxidant(s)" are used interchangeably herein.

Numerous cosmetic and medical treatments have been developed in an attempt to treat sensitive skin and related conditions. The condition of sensitive skin is evidenced as a tendency of the skin towards flushing and blushing. The skin disorder rosacea is an example of such a related condition. It is a common skin disorder that manifests itself, at different stages, as vivid skin redness, prominent vascularization, papules, pustules and swelling, as well as a predisposition to flushing and blushing. Rosacea is normally localized on the cheeks, chin, nose and forehead, but can also occur in the retroauricular areas, or on the chest, neck, back or scalp. Although the disorder has been observed in all age groups and in both genders, it is more common in women between the ages of 30 and 50 years. Also, it is most widespread in fair-skinned people.

The predisposition to flushing and blushing can be evoked by a variety of non-specific stimuli including UV light, heat, cold, chemical irritation, emotions, alcoholic beverages, spices, coffee and tea. In general, the rosacea-afflicted skin is abnormally sensitive to chemical and physical insults. The frequent flushing and blushing in rosacea eventually leads to permanent skin redness.

The exact mechanisms responsible for the flushing and blushing response in rosacea patients, and the cause of rosacea, are unknown. Several hypotheses have been put forward but none have taken root due to a dearth of scientific observations. It has been proposed that the causes of rosacea may be one or several of the following: (i) alimentary, (ii) psychological, (iii) pharmacological, (iv) infective, (v) climatic and (vi) immunological.

Current treatments for rosacea include the following:

(1) Antibiotics, such as topical tetracyclines, clindamycin, and erythromycin, have been used. Tetracycline is effective orally but not topically.

(2) Metronidazole has been used as a topically applied gel. Metronidazole 0.75% gel is sold under the trademark MetroGel. The gel has an effect on papules and pustules, but has been reported to be ineffective against skin redness, telangiectases or flushing.

(3) Drying lotions with 2% to 5% sulfur have been used to treat rosacea. Sulfur creams have obvious aesthetic disadvantages.

(4) Imidazole drugs, e.g. ketoconazole, have been shown useful to treat rosacea. These drugs are potent antimicrobial agents and the safety of their continuous use by chronic rosacea patients is questionable.

(5) Corticosteroid drugs are used only in severe cases. However, the potential side effects limit the duration and the skin area of corticosteroid treatment.

(6) Retinoids, such as 13-cis retinoic acid, (isotretinoin), have been used for systemic treatment of rosacea but with far greater risks of side effects than, for example, antibiotics.

2. Description of the Prior Art

In addition, various patents and patent applications address the treatment of rosacea and sensitive skin.

For example, U.S. Pat. No. 5,569,651 to Garrison et al., assigned to the assignee of the present application, teaches the use of formulations containing a combination of salicylic acid and lactic acid to address sensitive skin and rosacea.

European Patent Application No. EP 756,862 A1 to L'Oreal describes the use of bradykinin antagonists to treat sensitive skin and rosacea.

In European Patent No. 737,471 A2 to L'Oreal, the applicant claims that alkaline earth metal salts are beneficial in ameliorating rosacea.

European Patent Application No. 734,729 A1 to L'Oreal claims that a calcitonin gene related peptide antagonist is useful for treating rosacea of neurogenic origin when incorporated into topical formulations.

European Patent Application No. EP 722,928 A1 to Centre International de Recherches Dermatologiques Galderma claims that certain bicyclic aromatic compounds that affect cell proliferation are useful for treating a variety of skin conditions including rosacea.

Substance P antagonists in a topical formulation are claimed in European Patent Application No. EP 722,722 A1 to L'Oreal for treating "neurogenic skin reddening."

USSR Patent Application No. SU 1776411 A1 describes a method for treating rosacea by using trichopol and additional agiotropic preparations, and ointment containing trichopol, camphor oil, solutions of adrenaline and retinol acetate.

U.S. Pat. No. 5,438,073 to Saurat et al. claims the use of dermatological compositions containing retinoids for treatment of rosacea.

German Patent Application No. DE 4123615 A1 to Albert Weinberg proposes to treat rosacea with a cosmetic tonic containing amino acids.

A topical aqueous gel containing metronidazole and polyacrylic acid for treating rosacea is described in U.S. Pat. No. 4,837,378 to Borgman. A similar system is described in PCT Patent Application No. WO 88/06888 to Curatek Pharmaceuticals, Inc.

PCT Patent Application Publication No. WO 88/00465 to Schering Aktiengesellschaft Berlin und Bergkamen teaches the use of $C_7$–$C_{13}$ dicarboxylic acids, preferably azelaic acid, to treat rosacea.

PCT Patent Application Publication No. WO 93/20817 teaches a method of treating superficial inflammation associated with rosacea by topically applying compositions containing specific nitroimidazoles disclosed therein.

German Patent Application No. DE 3514724 A1 to Albin F. Jereb suggests that a combination of precipitated sulfur, vitamins, progesterone, testosterone propionate and menthol could lead to improvements in rosacea.

U.S. Pat. No. 4,133,893 to Spangler, describes the use for rosacea treatment of a topical formulation containing 1,1-dichloro-2-O-(-chlorophenyl)-2-(p-chlorophenyl)ethane.

Alternate treatments for rosacea and sensitive skin, that are more effective or that have fewer drawbacks, are needed.

SUMMARY OF THE INVENTION

Accordingly, it is an object of the present invention to provide a novel composition for treating rosacea.

It is another object of the present invention to provide such a composition that contains free radical scavengers.

It is still another object of the present invention to provide a novel method of treating rosacea.

It is a further object of the present invention to provide such a composition and method of application thereof that reduces the redness, flushing and blushing associated with either rosacea or sensitive skin, that is less irritating, less expensive, and derived from commonly available natural extracts.

To accomplish the foregoing objects and advantages, the present invention, in brief summary, is a composition that contains free radical scavengers to treat rosacea. The present invention also is a method of treating the tendency towards redness, flushing and blushing associated with rosacea or sensitive skin, by applying topically to skin the composition containing free radical scavengers.

BRIEF DESCRIPTION OF THE DRAWINGS

The foregoing and still other objects and advantages of the present invention will be more apparent from the following detailed explanation of the preferred embodiments of the invention in connection with the accompanying drawings wherein.

DESCRIPTION OF THE PREFERRED EMBODIMENTS

Figure 1:
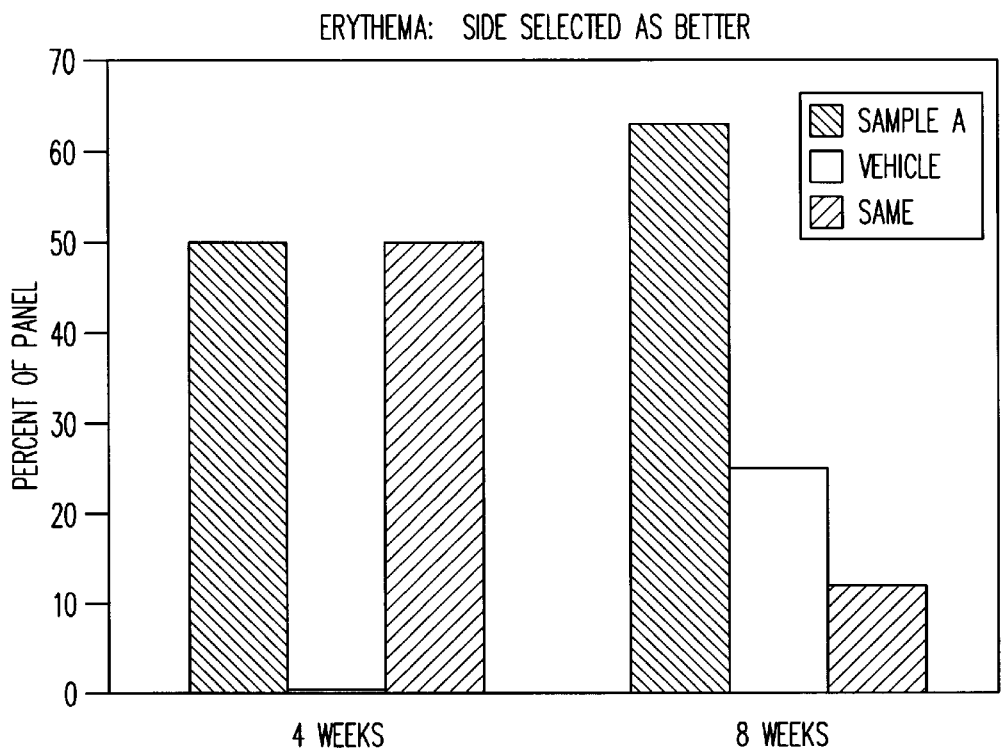
FIG. 1 illustrates graphically the results presented in Table 1.

The present invention is a composition that is capable of reacting with and quenching reactive small molecules that are both free radical and non-radical in nature. The composition contains at least one free radical scavenger. The present invention also includes a novel method of treating sensitive skin that manifests as a tendency towards redness, flushing and blushing. Additionally, the present invention includes a novel method of topically treating rosacea, a skin condition that also manifests as a tendency towards redness, flushing and blushing. The methods of treating either sensitive skin or rosacea include applying to the affected skin the present composition that contains free radical scavengers.

For the purposes of this invention, free radicals are defined as molecules having at least one unpaired electron in their molecular orbitals. Examples of such free radicals include atomic oxygen O, singlet oxygen $^1\Sigma_g{}^+O_2$, superoxide $O_2{}^-$ anion, nitric oxide NO., hydroxyl radical HO., alkoxy radicals R—O., alkyl radicals R., alkylperoxy radicals R—O—O., or sulphoxide radical R—S—O—O., where R is a carbon chain.

Also, for the purposes of this invention, the reactive non-radical molecules are defined as those molecules that do not have unpaired electrons but do have a populated anti-bonding molecular orbital leading to a weakness in the interatomic bonds, and a propensity to give rise to free radical reactive species. Examples of non-radical reactive small molecules include singlet oxygen $^1\Delta_gO_2$, peroxide ion $O_2{}^{2-}$ and its protonated form known as hydrogen peroxide $H_2O_2$, and ozone $O_3$.

An antioxidant is a molecule that can react with the reactive radical species and negate its chemical reactivity and/or can prevent generation of free radicals species from non-radical reactive species. For example, a compound that has a phenolic hydroxyl group can react with free radicals and form phenoxyradicals. These phenoxyradicals are significantly less reactive and less damaging to the biological systems because the energy of such radicals is lower due to the delocalization of the unpaired electron around the aromatic ring.

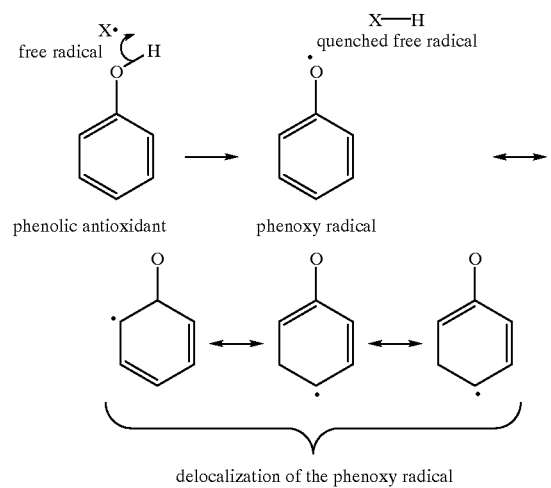

delocalization of the phenoxy radical

When ions of transition metals are present, formation of free radicals is catalyzed by such ions. A classic example is a Fenton reaction in which iron ions catalyze the generation of a hydroxy radical from hydrogen peroxide. Copper (I) salts are also thought to react with hydrogen peroxide to yield hydroxyradicals. In the presence of transition metals, some molecules exert their antioxidant action by chelating metal ions and making them unavailable for the catalysis of free radical formation.

It has now been discovered that the application of a topical formulation containing an antioxidant to skin reduces the redness, flushing and blushing associated with either sensitive skin or rosacea. The antioxidant or antioxidants useful to treat sensitive skin or rosacea can be selected from one or more of the following three groups.

I. Phenolic compounds that contain one or more hydroxyl groups (—OH) connected directly to a benzene ring and to another unsaturated chemical grouping. Preferred examples of such compounds include chlorogenic acid, caffeoylquinic acid, cinnamoylquinic acid, glabridin (also known as "PT-40"), bioflavonoids of flavone, isoflavone and flavonol structural type in both glycosilated and non-glycosilated forms, carnosic acid (also known as "lipid soluble rosemary extract" or "oxyless R"), naringenin, naringin, hesperetin, hesperedin, citrus bioflavenoid complexes, quercetin, rutin, ellagic acid, tocopherols and their derivatives (for example, vitamin E Succinate 1000 PEG), ascorbic acid and its derivatives, propyl gallate, sylibin (also known as "silymarin"), cycloartenyl ferrulate, gamma-oryzanol, butylated hydroxytoluene and caffeic acid.

II. Sulfur-containing compounds that contain one or more sulfhydryl groups (-SH) or one or more disulfide groups (—S—S—). Preferred examples of such sulfhydryl compounds include glutathione, cysteine, N-acetyl cysteine, alpha-lipoic acid, dihydrolipoic acid and thiolactic acid.

III. Polyene compounds that have conjugated systems of double bonds. Preferred examples of such polyene compounds include sorbic acid, carotenoids, b-carotene, lycopene and lutein.

Unless otherwise specified, for purposes of the present invention the term "compound" is meant as "a single chemical entity," as opposed to "a combination of two or more elements," which is a typical dictionary definition of the word "compound."

It is believed that the effect of the free radical scavenger will be synergistically improved when combined with a humectant, an emollient or an antiinflammatory.

The addition of humectants and emollients to the antioxidant composition is expected to aid in the rehydration and maintenance of hydration of the treated skin. Improved hydration of the skin is believed to both increase the absorbence of the free radical scavenger by the skin and augment the delivery of the free radical scavenger to the active site.

It is contemplated that conventional emollients known it the art may be used. Examples of these emollients are: mineral oil, petrolatum, paraffin, ceresin, ozokerite, microcrystalline wax, perhydrosqualene dimethyl polysiloxanes, methylphenyl polysiloxanes, silicone, silicone-glycol copolymers, triglyceride esters, acetylated monoglycerides, ethoxylated glycerides, alkyl esters of fatty acids, fatty acids and alcohols, lanolin and lanolin derivatives, polyhydric alcohol esters, sterols, beeswax derivatives, polyhydric alcohols and polyethers, and amides of fatty acids. Other suitable emollients can be found in Sagarin, *Cosmetics, Science and Technology,* 2nd Ed., vol. 1, pp. 32–43 (1972), which is incorporated herein by reference. Although various emollients known in the art would be useful in the present invention, the preferred emollient is silicone.

Humectants known in the art to increase skin hydration when applied topically, such as polyhydric alcohols, are appropriate. Examples of suitable humectants are: glycerin, propylene glycol, butylene glycol, diglycerol, or ester derivatives thereof. However, the preferred humectant is glycerin.

Any antiinflammatory known in the art to be suitable for topical application would be appropriate for use in the present invention. It is believed that the addition of an antiinflammatory will also increase absorbency and facilitate delivery of the antioxidant to the active site. The antiinflammatories contemplated for combination with the antioxidant can be either steroidal or non-steroidal. Steroidal antiinflammatories are preferred for more severe cases of rosacea. Non-steroidal antiinflammatories are preferred for less severe cases of rosacea. The preferred antiinflammatories are those antiinflammatories that inhibit enzymes involved in inflammatory cascades. For example, preferred antiinflammatories would be those that inhibit phospholipase A2, cyclooxygenase, and lipoxygenase. Most preferred are antiinflammatories that inhibit lipoxygenase. It is believed that it is the products of lipoxygenase action that are of primary importance in skin inflammation. In addition, it is believed that antiinflammatories that function by inhibiting platelet aggregating factors will also produce synergistic results when combined with an antioxidant from Group I, II, or III above. Examples of preferred antiinflammatories are hydrocortisone, boswellic acid or extracts of Boswellia serrata, indomethacin, salicylic acid, acetyl salicylic acid and other salicylic acid derivatives. The more preferred of these antiinflammatories are boswellic acid and salicylic acid derivatives since these antiinflammatories are known to have excellent compatibility with the skin.

Furthermore, combining antioxidants from at least two of the antioxidant Groups I, II and III above, is also believed to yield synergistic results. It is also expected that synergism may be achieved by combining a lipophilic antioxidant with a hydrophilic antioxidant from one of the Groups I, II, and III defined above. Examples of lipophilic antioxidants contemplated are glabridin (Group I), tocopherols (Group I), cyloartenyl ferrulate (Group I), gamma-oryzanol (Group I), alpha-lipoic acid (Group II) and sorbic acid (Group III). Examples of hydrophilic antioxidants contemplated are ascorbic acid (Group I), isoflavone and flavonol structural types in glycosilated forms (Group I), glutathione (Group II) and n-acetyl cysteine (Group II). It is preferred that each antioxidant in the hydrophilic/lipophilic blend is selected from a separate antioxidant group. In a preferred embodiment of the hydrophilic/lipophilic blend, the hydrophilic antioxidant is ascorbic acid and the lipophilic antioxidant is α-tocopherol (or vitamin E).

A "suitable vehicle" means drugs, cosmetics, medicaments or inert ingredients that are suitable for use in direct contact with human tissues without undue toxicity. For example, a suitable vehicle may be a cream, gel, ointment, lotion, patch, tape, stick or spray.

Three examples of vehicles expected to be suitable for use in the present invention are as follows.

Vehicle 1 includes (a) about 2 wt % to about 10 wt % glycerin, (b) about 1 wt % to about 10 wt % propylene glycol, (c) about 0.1 wt % to about 2 wt % hydroxyethyl cellulose, (d) about 0.1 wt % to about 1 wt % imidazolidilyl urea, and (e) about 0.01 wt % to about 2 wt % disodium-EDTA.

Vehicle 2 includes (a) about 1 wt % to about 10 wt % glycerin, (b) about 1 wt % to about 10 wt % propylene glycol, (c) about 1 wt % to about 10 wt % octyl palmitate, (d) about 1 wt % to about 10 wt % myristyl myristate, (e) about 1 wt % to about 6 wt % cetearyl alcohol/Ceteareth-20, (f) about 0.5 wt % to about 6 wt % glyceryl monostearate, (g) about 0.1 wt % to about 2 wt % hydroxyethyl cellulose, (h) about 0.1 wt % to about 1 wt % imidazolidilyl urea, (i) about 0.05 wt % to about 0.5 wt % methyl paraben, and (j) about 0.01 wt % to about 2 wt % disodium-EDTA.

Vehicle 3 includes (a) about 2 wt % to about 10 wt % glycerin, (b) about 1 wt % to about 10 wt % octyl palmitate, (c) about 1 wt % to about 10 wt % myristyl myristate, (d) about 1 wt % to about 7 wt % cetearyl alcohol/Ceteareth-20, (e) about 1 wt % to about 10 wt % propylene glycol, (f) about 1 wt % to about 6 wt % glyceryl monostearate, (g) about 0.1 wt % to about 2 wt % hydroxyethyl cellulose, (h) about 0.1 wt % to about 1 wt % imidazolidilyl urea, (i) about 0.05 wt % to about 0.5 wt % methyl paraben, and (j) about 0.01 wt % to about 2 wt % disodium-EDTA.

The topical antioxidant compositions of the present invention may contain a single antioxidant, or a combination of antioxidants, thus an antioxidant blend. The term "antioxidant" as used herein is intended to encompass both a single antioxidant as well as an antioxidant blend. It is contemplated that the final composition contains a total concentration of antioxidant, whether as a single antioxidant or as an antioxidant blend, that ranges from about 0.001 wt % to about 100 wt %. The antioxidant may also be incorporated into various vehicles to facilitate topical application. If a vehicle other than a cream, emulsion, lotion or gel is used, then it is contemplated that the concentration of antioxidant would range from about 0.001 wt % to about 99 wt %.

For practical reasons, creams, emulsions, lotions or gels would require concentrations of antioxidant that are less than 50 wt %. Formulations having concentrations of antioxidants greater than 50 wt % would not be aesthetically pleasing, or physically stable, as creams, emulsions, lotions or gels.

Of course, the concentration of antioxidant in any topical composition will vary depending upon the specific antioxidant used. It is well known in the art that various chemicals exhibit antioxidant properties at different concentrations depending upon the relative potency of that particular chemical. Likewise, it is also well known in the art that various chemicals will exhibit negative, undesired effects at different relative concentrations.

However, as indicated above, it is contemplated that in order to obtain elegant, topical compositions in the form of creams, emulsions, lotions, or gels, such compositions may include from about 0.001 wt % to about 50 wt % of an antioxidant. Preferably, these topical compositions include from about 0.001 wt % to about 20 wt % of antioxidant. Most preferably, such compositions contain about 2 wt % to about 20 wt %. These are the contemplated concentrations for total antioxidant utilized. A topical composition of the present invention may be a combination of two or more antioxidants. When a combination of antioxidants is used, the concentration of each individual antioxidant may be less than 0.001 wt %, but the total concentration of antioxidants should be from 1 wt % to about 50 wt %, preferably from 1 wt % to about 20 wt %, and most preferably from about 2 wt % to about 20 wt %.

When the vehicle is a patch, tape, spray or stick, the concentration of antioxidant is from about 0.001 wt % to about 99 wt %. Preferably, the concentration of antioxidant is from about 2 wt % to about 99 wt %. More preferably the concentration of antioxidant is from 10 wt % to about 99 wt %. Most preferably, the concentration of antioxidant is from about 20 wt % to 99 wt %.

The topical compositions of the present invention can be made as lotions. A first or more basic lotion includes about 0.1 wt % to about 50 wt %, preferably from about 1 wt % to about 20 wt %, and most preferably about 2 wt % to about 20 wt % of the antioxidant, and the remainder water. A second lotion includes: about 0.1 wt % to about 50 wt %, preferably from about 1 wt % to about 20 wt %, and most preferably about 2 wt % to about 20 wt % of the antioxidant; about 0.5 wt % to about 50 wt % of an emollient; about 0.1 wt % to about 30 wt % of an emulsifier; and, the remainder water. The second lotion may also include: up to about 10 wt % of a preservative; from about 0.1 wt % to about 3 wt % of a fragrance; and up to about 5 wt % of a dye or a pigment. A third lotion includes: about 0.1 wt % to about 50 wt %, preferably from about 1 wt % to about 20 wt %, and most preferably about 2 wt % to about 20 wt % of the antioxidant; about 5.0 wt % to about 15 wt % of an emollient; about 1 wt % to about 3 wt % of an emulsifier; about 0.1 wt % to 0.8 wt % of a thickener; about 0.5 wt % to 1 wt % of a preservative; and, the remainder water.

The topical composition of the invention can also be formulated as a cream. A first or more basic cream includes: about 0.1 wt % to about 50 wt %, preferably from about 1 wt % to about 20 wt %, and most preferably about 2 wt % to about 20 wt % of the antioxidant; from about 0.5 wt % to about 50 wt % of an emollient; about 0.1 wt % to about 6 wt % of a thickener; and the remainder water. A second, preferred cream includes: about 0.1 wt % to about 50 wt %, preferably from about 1 wt % to about 20 wt %, and most preferably about 2 wt % to about 20 wt % of the antioxidant; from about 0.5 wt % to about 50 wt % of an emollient; about 0.1 wt % to about 30 wt % of an emulsifier; about 0.1 wt % to about 6 wt % of a thickener; and, the remainder water. A third preferred cream includes: about 0.1 wt % to about 50 wt %, preferably from about 1 wt % to about 20 wt %, and most preferably about 2 wt % to about 20 wt % of the antioxidant; 10 wt % to 30 wt % of an emollient; 3 wt % to 5 wt % of an emulsifier; 1.0 wt % to 5 wt % of a preservative; 0.5 wt % to 1.0 wt % of a thickener; and, the remainder water.

Also as stated above, the antioxidant can be combined with most conventional emollients, examples of which have been listed above.

The radical scavenger can be combined with most emulsifiers that are used to make lotions, creams and other suitable topical vehicles. The emulsifiers can be cationic, anionic, nonionic, amphoteric, or a combination thereof. Nonionic emulsifiers are preferred. Exemplary nonionic emulsifiers are commercially available sorbitans, alkoxylated fatty alcohols and alkyl polyglycosides. Anionic emulsifiers may include soaps, alkyl sulfates, monoalkyl and dialkyl phosphates, alkyl sulphonates and acyl isothionates. An examples of an amphoteric emulsifier that may be used is lactamidopropyl trimonium chloride. Other suitable emulsifiers can be found in McCutcheon, *Detergents and Emulsifiers,* North American Edition, pp. 317–324 (1986), which is incorporated herein by reference.

Suitable vehicles for the present invention may also contain thickeners. Examples of suitable thickeners include cellulose derivatives, such as hydroxyethyl cellulose and hydroxypropyl cellulose, as well as polyacrylic acid polymers.

Examples of preservatives that are suitable for use with the present antioxidant compositions include: alkanols, especially ethanol and benzyl alcohol; parabens; sorbates; urea derivatives; and, isothiazolinones.

Lotions or creams that incorporate an antioxidant of the present invention can be made using conventional homogenization methods known to those skilled in the art. It is also possible to use a process of microfluidization that involves co-mixing the aqueous phase and the oil phase of such creams and lotions in a high-pressure homogenizer that reduces the emulsion particle size dramatically to about 1/400th the size of those in creams and lotions prepared without applying high pressure. Microfluidization allows one to prepare elegant stable creams and lotions containing effective amounts of a antioxidant without the use of traditional emulsifiers and surfactants.

The topical compositions of the present invention can also be formulated as a micro-emulsion, which is a subcategory of emulsions. A first, basic micro-emulsion system includes about 0.1 wt % to about 50 wt %, preferably from about 1 wt % to about 20 wt %, and most preferably about 2 wt % to about 20 wt % of the antioxidant; about 0.5 wt % to about 20 wt % of a hydrocarbon; about 0.5 wt % to about 20 wt % of an oil; and, the remainder water. A second, more preferred micro-emulsion system includes about 2.0 wt % to about 20 wt % of the antioxidant; about 0.5 wt % to about 15 wt % of a hydrocarbon; about 1 wt % to about 15 wt % of an oil; about 0.1 wt % to about 10 wt % of a fatty alcohol; up to 30 wt % of an nonionic surfactant; and, the remainder water.

Hydrocarbons of the formula $C_nH_{2n+2}$, where n is an integer between 10 and 20, may be used. The hydrocarbons may be straight chains, branched or cyclic. Preferably, a straight chain hydrocarbon having n=2 is used. Examples of oils that may be used are mineral oil and silicone oil. Examples of alcohols that may be used are cetyl alcohol, isostearyl alcohol, stearyl alcohol, dodecanol and dodecenol. Nonionic surfactants may be fatty esters, esters of fatty alcohols or ethoxylated alcohols. Examples of nonionic surfactants are polyethylene glycol, isopropyl myristate, cetyl isooctadecanoate, polypropylene glycols, sorbitants and isopropyl oleate.

The topical compositions of the invention can be formulated as oil-in-water or water-in-oil emulsions. The compositions can also be in the form of a multiphase emulsion, such as a water-in-oil-in-water type emulsion as disclosed in U.S. Pat. No. 4,254,105, incorporated herein by reference. The compositions of the invention can also be formulated as triple emulsions of the oil-in-water-silicone fluid type disclosed in U.S. Pat. No. 4,960,764, incorporated herein by reference.

The compositions of the invention can also be made as a liposomal formulation, for example, according to the methods described in Mezei, *J. Pharmaceut. Pharmacol.*, vol. 34, pp. 473–474 (1982), or modification thereof. In such compositions, droplets of the antioxidant solution can be entrapped inside the liposomal vesicles with the shell of the liposome being a phospholipid or other suitable lipids (e.g. skin lipids). To form a topical composition, the liposomes can then be added to any carrier system described above according, for example, to the preparation modes, uses and compositions of topical liposomes described in Mezei, *Topics in Pharmaceutical Sciences,* Breimer et al. Eds., pp. 345–358, Elsevier Science Publishers BV, New York (1985), or according to the reverse-phase evaporation method described in Szoka et al., *Proc. Nat. Acad. Sciences,* vol. 75, pp. 4194–4198 (1978), and Diploses et al., *J. Soc. Cosmetic Chemists,* vol. 43, pp. 93–100 (1992), all three of which are incorporated herein by reference. Solutions of antioxidants can also be entrapped in polymeric vesicles with a shell consisting of a suitable polymeric material, such as gelatin, cross-linked gelatin, polyamide, polyacrylates and the like to form a vesicle that is then incorporated into the topical composition.

Thus, to practice the present invention antioxidant compositions may include only a single antioxidant, a combination of antioxidants, or one or more antioxidants in combination with other cosmetic and pharmaceutical actives and excipients. As stated before, the effect of the antioxidant may be synergized when combined with certain humectants, such as glycerin, certain emollients, such as silicone, as well as with anti-inflammatories. Combining antioxidants among and within Formulas I, II and III is also expected to yield synergistic results.

The following examples are compositions that are contemplated to be in terms of the present invention for the treatment of rosacea.

| Ingredient | Type of Vehicle and Wt % of Ingredient Therein | | |
|---|---|---|---|
| | Cream | Lotion | Gel |
| Magnesium ascorbyl phosphate | 3.00 | 3.25 | 2.00 |
| Tocopherol | 1.00 | 1.00 | 0.01 |
| Sylibilin | 0.05 | 0.01 | 0.01 |
| Hesperetin | 1.00 | 0.40 | 0.02 |
| Naringenin | 1.50 | 0.75 | 0.10 |
| Butylated hydroxytoluene | 0.10 | 0.07 | 0.01 |
| Lipoic acid | 1.00 | 1.00 | 0.50 |

-continued

| Ingredient | Type of Vehicle and Wt % of Ingredient Therein | | |
|---|---|---|---|
| | Cream | Lotion | Gel |
| Vitamin E succinate PEG1000 | 2.50 | 1.70 | 1.00 |
| Cholesterol | 0.20 | 0.15 | 0.05 |
| Carbopol 934 | 0.25 | — | 0.75 |
| Carbopol 941 | — | 0.25 | — |
| Xanthan Gum | 0.10 | 0.10 | — |
| Glycerine | 5.00 | 5.00 | 1.50 |
| Poltassium hydroxide | 0.25 | 0.25 | 0.65 |
| Glyceryl monostearate | 2.50 | 1.50 | — |
| Cetyl alcohol | 2.00 | 1.00 | — |
| Myristyl myristate | 2.00 | 2.00 | — |
| PEG40 stearate | 2.00 | 1.50 | — |
| Soya sterols | 1.00 | 0.25 | — |
| PEG 24 cholesteryl ether | 0.60 | 0.30 | — |
| Silica | 0.35 | 0.30 | — |
| Propylparaben | 0.40 | 0.40 | 0.25 |
| Dioctyl maleate | 2.55 | 2.50 | 0.50 |
| Grape seed oil | 2.10 | 2.70 | 0.60 |
| Sunflower seed oil | 2.13 | 2.50 | 0.50 |
| Squalene | 1.80 | 2.00 | — |
| corn starch | 1.90 | 1.00 | — |
| Zeolite | 0.87 | 0.60 | 0.25 |
| Sodium citrate | 1.00 | 1.00 | — |
| citric acid | 0.25 | 0.25 | — |
| tetrasoldium EDTA | 0.20 | 0.15 | 0.01 |
| Imadazolidinyl urea | 0.50 | 0.40 | 0.50 |
| Cyclomethicone tetramer | 2.60 | 2.00 | — |
| Benzyl alcohol | 0.50 | 0.40 | 0.50 |
| Fragrances | 0.30 | 0.25 | 0.10 |
| Polysorbate 20 | — | — | 1.50 |
| Vehicle | qs | qs | qs |

A second example of a cream that is expected to be useful for the treatment of rosacea is as follows:

| Ingredient | Wt % |
|---|---|
| Tocopherol | 2.0 |
| Quercetin | 2.5 |
| Lycopene | 5.0 |
| Carbopol | 0.3 |
| Triethanolamine | 0.5 |
| Mineral oil | 1.5 |
| Safflower oil | 0.3 |
| Squalene | 1.7 |
| Dimethicone | 0.7 |
| Allantoin | 1.0 |
| Oleyl alcohol | 0.6 |
| Cholesterol | 4.5 |
| Lanolin oil | 0.6 |
| Water | qs |

An example of a moisturizing cream that is contemplated for use in the treatment of rosacea is as follows:

| Ingredient | Wt % |
|---|---|
| Propyl gallate | 1.00 |
| Rosmarinic acid | 5.00 |
| N-acetyl-cysteine | 3.50 |
| Beta-carotene | 0.001 |
| Licorice root extract | 0.01 |
| Naringenin | 2.70 |
| PPG Myristyl Ether Propionate | 6.50 |
| Oleyl alcohol | 3.50 |
| Stearic acid | 8.60 |
| Lanolin | 1.00 |
| Glycerine | 2.50 |
| Triethanolamine | 0.50 |
| Germal | 0.10 |

-continued

| Ingredient | Wt % |
|---|---|
| Methyl paraben | 0.01 |
| Water | qs |

An example of a moisturizing cream contemplated for use in-the treatment of rosacea is as follows:

| Ingredient | Wt % |
|---|---|
| Gamma-oryzanol | 1.50 |
| Ellagic acid | 0.10 |
| Glutatione | 0.50 |
| Lipoic acid | 0.30 |
| Behitrimonium methosulfate | 1.20 |
| Stearyl alcohol | 1.00 |
| PPG myristyl etherprpionate | 0.70 |
| Pentaerythrityl tetracaprylate | 1.00 |
| Petrolatum | 2.50 |
| Dimethicone | 0.75 |
| Hydrolyzed wheat protein | 1.60 |
| Methyl paraben | 0.10 |
| Fragrance | 0.03 |
| Propylene glycol | 2.00 |
| Glycerine | 1.00 |
| Water | qs |

EXAMPLE 1

An eight week double-blind clinical study was conducted to determine the efficacy of an antioxidant blend (Sample A) as compared to a non-antioxidant blend (Control) to treat two skin conditions associated with rosacea: erythema and flushing/blushing.

| Active Ingredients | Percentage |
|---|---|
| SAMPLE A | |
| Mixed Tocopherols | 1.0 |
| Vit E succinate 1000 PEG | 0.5 |
| Gamma Oryzanol | 0.2 |
| Lipoic Acid | 0.1 |
| Hesperetin | 0.1 |
| Naringenin | 0.1 |
| Silybin (Silymarin) | 0.1 |
| Chlorogenic Acid | 0.01 |
| VEHICLE | 97.89 |
| | 100.00 |
| CONTROL | |
| Vehicle | 100 wt % |

There are four stages of rosacea, as well as a predisposition to the condition. The stages are defined as follows:

Pre-rosacea- skin flushes easily and redness lasts longer than normal and there is a family history of the condition.

STAGE I: Frequent flushing, some persistent erythema

STAGE II: Persistent erythema and telangiectasias

STAGE III: Papules and pustules (plus Stage II)

STAGE IV: Rhinophyma (bumpy, bulbous nose)

Sixteen women having rosacea classified as either stage I or stage II, participated in the study. Subjects were asked to apply Sample A to one side of their face and the Control to the other side of their face. For the first two weeks of the trial, subjects applied Sample A and the Control once daily to minimize adverse reactions. Thereafter, the number of daily applications was increased to twice daily, morning and evening, for the remainder of the eight week trial period.

A physician assessed the patients at the beginning of the study to establish a baseline. The physician then reassessed the patients at four weeks and then at eight weeks of the trial period. At each time point, the patients were assessed for erythema and for their flushing/blushing response. The flushing/blushing response was usually triggered by asking the patient the question "Do you turn red easily." For each attribute, the physician selected the side of the face that appeared less symptomatic. Additionally, the degree of difference between each side was rated on a scale of 1 (slight difference) to 6 (dramatic difference).

TABLE 1

| Side Of Face Exhibiting Less Erythema | | |
|---|---|---|
| | Four Weeks | Eight Weeks |
| Sample A Side Less | 50% | 63% |
| Control Side Less | 0% | 25% |
| Both Sides Equal | 50% | 12% |

FIG. 1 illustrates graphically the results presented in Table 1.

TABLE 2

Magnitude of Difference in Erythema Between Sample A Side and Control Side

| | Percentage of Panelists | |
|---|---|---|
| Difference | Four weeks | Eight weeks |
| Moderate/Dramatic (5) | 0 | 6% |
| Moderate (4) | 0 | 6% |
| Slight to Moderate (3) | 25% | 25% |
| Slight (2) | 19% | 25% |
| Very Slight (1) | 6% | 0 |
| No Difference | 50% | 12% |
| Control-Very Slight (−1) | 0 | 6% |
| Control-Slight (−2) | 0 | 19% |
| Control-Slight to Moderate (−3) | 0 | 0 |

TABLE 3

| Side Of Face Exhibiting Less Flushing | | |
|---|---|---|
| | Four Weeks | Eight Weeks |
| Sample A Side Less | 31% | 50% |
| Control Side Less | 0% | 19% |
| Both Sides Equal | 69% | 31% |

Figure 2:
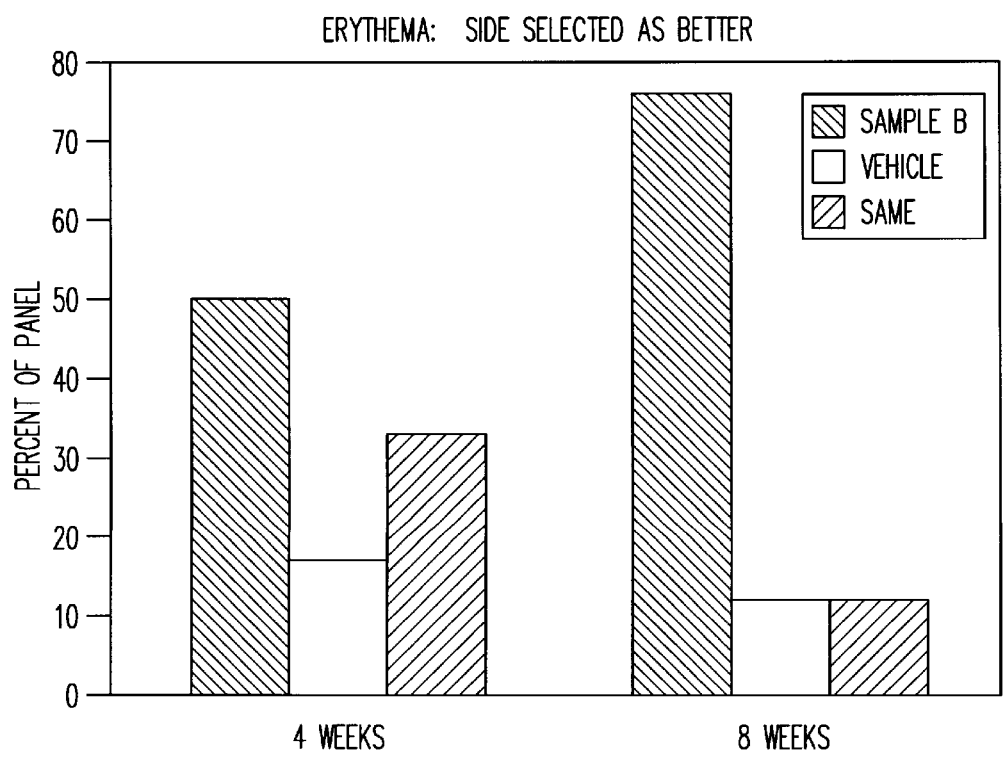
FIG. 2 illustrates graphically the results presented in Table 3.

FIG. 2 illustrates graphically the results presented in Table 3.

TABLE 4

Magnitude of Difference in Flushing Between Sample A Side and Control Side

| | Percentage of Panelists | |
|---|---|---|
| Difference | Four weeks | Eight weeks |
| Moderate | 0 | 12% |
| Slight to Moderate (3) | 6% | 6% |
| Slight (2) | 25% | 25% |
| Very Slight (1) | 0% | 0 |

TABLE 4-continued

Magnitude of Difference in Flushing Between
Sample A Side and Control Side

|  | Percentage of Panelists | |
| --- | --- | --- |
| Difference | Four weeks | Eight weeks |
| No Difference | 69% | 31% |
| Control-Very Slight (−1) | 0 | 0% |
| Control-Slight (−2) | 0 | 19% |

It is evident from these results that patients treated with Sample A exhibited noticeable, as well as unexpected, improvements in both erythema and flushing. The improvements resulting from application of Sample A are statistically significant in comparison to the results achieved with the control which contained only the vehicle.

EXAMPLE 2

The protocol utilized for the clinical testing of Example 2 is the same protocol utilized for Example 1, described above, but with a different antioxidant blend (Sample B). However, seventeen subjects were tested.

| Active Ingredient | Percentage |
| --- | --- |
| SAMPLE B | |
| Tocopherol Acetate | 1.0 |
| Vitamin E Succinate 1000 PEG | 0.5 |
| Gamma Oryzanol | 0.2 |
| Carnosic Acid | 0.2 |
| Butylated hydroxytoluene | 0.15 |
| Propyl gallate | 0.1 |
| Silybin (Silymarin) | 0.1 |
| Chlorogenic acid | 0.01 |
| Glabridin | 0.005 |
| Citrus Bioflavonoid Complex | 0.001 |
| VEHICLE | 97.734 |
| TOTAL | 100.000 |
| CONTROL | |
| Vehicle | 100 wt % |

TABLE 5

Side Of Face Exhibiting Less Erythema

|  | Four Weeks | Eight Weeks |
| --- | --- | --- |
| Sample B Side Less | 50% | 76% |
| Control Side Less | 17% | 12% |
| Both Sides Equal | 33% | 12% |

Figure 3:
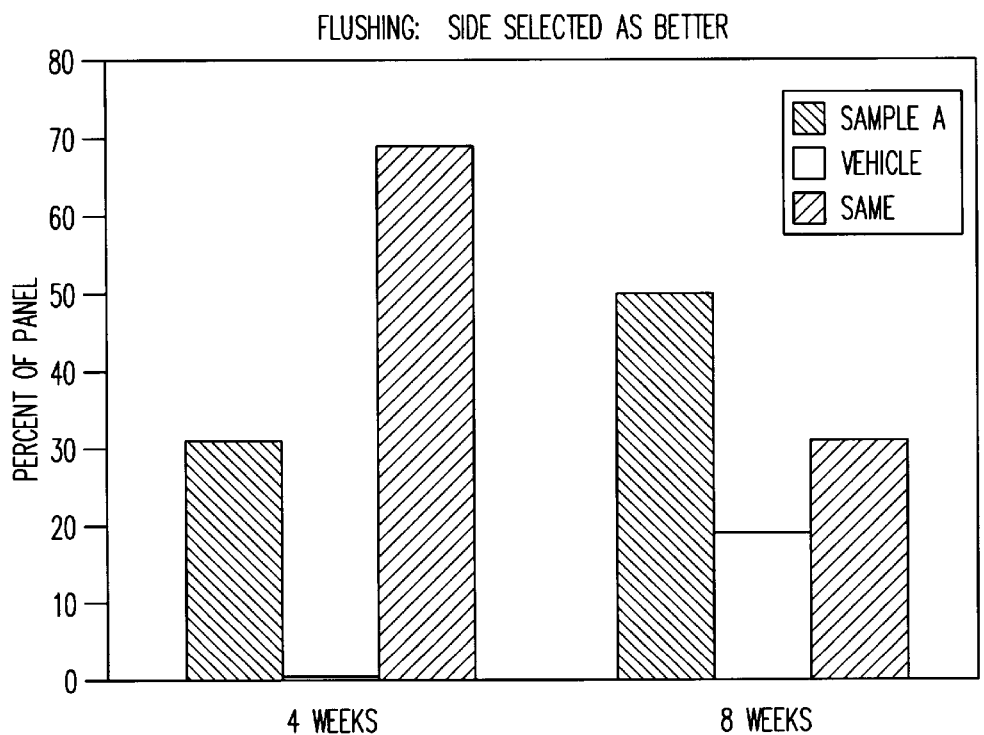
FIG. 3 illustrates graphically the results presented in Table 5.

FIG. 3 illustrates graphically the results presented in Table 5.

TABLE 6

Magnitude of Difference in Erythema Between
Sample B Side and Control Side

|  | Percentage of Panelists | |
| --- | --- | --- |
| Difference | Four weeks | Eight weeks |
| Moderate/Dramatic (5) | 0 | 6% |
| Moderate (4) | 0 | 6% |

TABLE 6-continued

Magnitude of Difference in Erythema Between
Sample B Side and Control Side

|  | Percentage of Panelists | |
| --- | --- | --- |
| Difference | Four weeks | Eight weeks |
| Slight to Moderate (3) | 25% | 25% |
| Slight (2) | 19% | 25% |
| Very Slight (1) | 6% | 0 |
| No Difference | 50% | 12% |
| Control-Very Slight (−1) | 0 | 6% |
| Control-Slight (−2) | 0 | 19% |
| Control-Slight to Moderate −(3) | 0 | 0 |

TABLE 7

Side Of Face Exhibiting Less Flushing

|  | Four Weeks | Eight Weeks |
| --- | --- | --- |
| Sample B Side Less | 29% | 71% |
| Control Side Less | 6% | 12% |
| Both Sides Equal | 65% | 18% |

Figure 4:
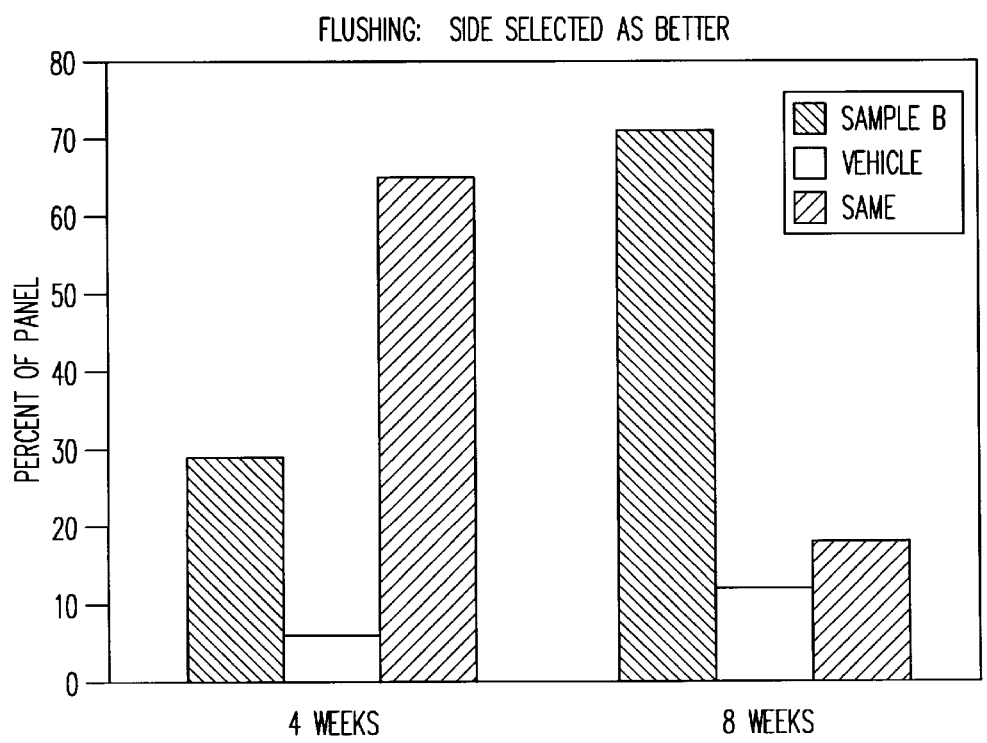
FIG. 4 illustrates graphically the results presented in Table 7.

FIG. 4 illustrates graphically the results presented in Table 7.

TABLE 8

Magnitude of Difference in Flushing Between
Sample B Side and Control Side

|  | Percentage of Panelists | |
| --- | --- | --- |
| Difference | Four weeks | Eight weeks |
| Moderate (4) | 0 | 0% |
| Slight to Moderate (3) | 11% | 24% |
| Slight (2) | 29% | 47% |
| Very Slight (1) | 0% | 0 |
| No Difference | 71% | 18% |
| Control-Very Slight (−1) | 0 | 0% |
| Control-Slight (−2) | 6% | 12% |

As in the case of Sample A, above, it is also evident that patients treated with Sample B exhibited noticeable improvements in both erythema and flushing. The improvements resulting from application of Sample B are statistically significant when compared to the results achieved with the Control.

Of the foregoing two samples (Sample A and Sample B), the cream of Sample B is preferred. During formulation of any antioxidant composition, excessive heat should be avoided. Formulation of the foregoing compositions, whether lotions, creams, gels or other cosmetically acceptable types, is according to common formulation techniques known in the art.

Various modifications may be made to the compositions and methods of the present invention, as will be apparent to those skilled in the art. Thus, it will be obvious to one of ordinary skill in the art that the foregoing description is merely illustrative of certain preferred embodiments of the present invention, and that various obvious modifications can be made to these embodiments.

What is claimed is:

1. A method of treating rosacea or flushing and/or blushing associated therewith comprising topically applying to an individual in need thereof a composition comprising an effective amount of an antioxidant selected from the group consisting of a phenolic compound, sulfur-containing compound, polyene compound, and mixtures thereof, wherein said phenolic compound contains at least one hydroxyl group connected directly to a benzene ring, wherein said sulfur-containing compound contains at least one sulfhydryl group or at least one disulfide group, and wherein said polyene compound has conjugated systems of double bonds.

2. The method of claim 1, wherein said composition comprises from about 0.001 to about 99 weight percent of said antioxidant and further comprises a vehicle.

3. The method of claim 2, wherein said composition comprises from about 0.001 to about 50 weight percent of said antioxidant and said vehicle is selected from the group consisting of a lotion, a gel, a cream and an emulsion.

4. The method of claim 2, wherein said composition comprises from about 0.001 to about 20 weight percent of said antioxidant.

5. The method of claim 2, wherein said composition comprises from about 2 to about 20 weight percent of said antioxidant.

6. The method of claim 1, wherein said antioxidant is selected from the group consisting of chlorogenic acid, caffeoylquinic acid, cinnamoylquinic acid, glabridin, carnosic acid, naringenin, naringin, hesperetin, hesperedin, quercetin, rutin, ellagic acid, tocopherols, tocopherol derivatives, vitamin E succinate 1000 PEG, propyl gallate, sylibin, gamma-oryzanol, caffeic acid, glutathione, cysteine, N-acetyl cysteine, alpha-lipoic acid, dihydrolipoic acid, thiolactic acid, carotenoids, b-carotene, lutein, lycopene, sorbic acids and a combination of one or more thereof.

7. The method of claim 1, wherein said composition is applied up to two times a day.

8. The method according to claim 2, further comprising at least one compound selected from the group consisting of an emollient, a humectant and an antiinflammatory.

9. A composition for treating rosacea or flushing and/or blushing associated therewith comprising:

about 2 wt % antioxidant, and about 98 wt % vehicle, wherein said antioxidant comprises a mixture of tocopherols, vitamin E succinate 1000 PEG, gamma oryzanol, lipoic acid, hesperetin, naringenin, silybin and acid.

10. The composition of claim 9, wherein said mixture comprises:

about 1 wt % tocopherols, about 0.5 wt % vitamin E succinate 1000 PEG, about 0.2 wt % gamma oryzanol, about 0.1 wt % lipoic acid, about 0.1 wt % hesperetin, about 0.1 wt % naringenin, about 0.1 wt % silybin, and about 0.01 chlorogenic acid.

11. A composition for treating rosacea or flushing and/or blushing associated therewith comprising:

about 2 wt % antioxidant, and about 98 wt % vehicle, wherein said antioxidant comprises a mixture of tocopherol acetate, vitamin E succinate 1000 PEG, gamma oryzanol, carnosic acid, butylated hydroxytoluene, propyl gallate, silybin, chlorogenic acid, glabridin, and citrus bioflavonoid complex.

12. The composition of claim 11 wherein said mixture comprises:

about 1 wt % tocopherol acetate, about 0.5 wt % vitamin E succinate 1000 PEG, about 0.2 wt % gamma oryzanol, about 0.2 wt % carnosic acid, about 0.15 wt % butylated hydroxytoluene, about 0.1 wt % propyl gallate, about 0.1 wt % silybin, about 0.01 wt % chlorogenic acid, about 0.005 wt % glabridin, and about 0.001 wt % citrus bioflavonoid complex.

13. The method of claim 1, wherein said antioxidant is said phenolic compound.

14. The method of claim 1, wherein said antioxidant is said sulfur-containing compound.

15. The method of claim 1, wherein said antioxidant is said polyene compound.

16. The method of claim 1, wherein said effective amount is from about 0.001 to 100 weight percent of said composition.

17. A method for treating rosacea or flushing and/or blushing associated therewith, comprising topically applying to an individual in need thereof a composition comprising an effective amount of an antioxidant selected from the group consisting of bioflavanoids of flavone, isoflavone or flavanol, citrus bioflavanoid complexes, ascorbic acid, ascorbic acid derivatives and cycloartenyl ferrulate.

18. A method for treating rosacea or flushing and/or blushing associated therewith, comprising topically applying to an individual in need thereof a composition comprising an effective amount of an antioxidant and a vehicle, wherein said antioxidant comprises a mixture of at least two compounds, each of said at least two compounds being selected from the group consisting of phenolic compounds that contain at least one hydroxyl group connected directly to a benzene ring, sulfur-containing compounds that contain at least one sulfhydryl group or at least one disulfide group, and polyene compounds that have conjugated systems of double bonds; and wherein the first of said at least two compounds is different than the second of said at least two compounds.

19. A method for treating rosacea or flushing and/or blushing associated therewith, comprising topically applying to an individual in need thereof a composition comprising an effective amount of an antioxidant and a vehicle, wherein said antioxidant comprises a mixture of at least two compounds, each of said at least two compounds being selected from the group consisting of phenolic compounds that contain at least one hydroxyl group connected directly to a benzene ring, sulfur-containing compounds that contain at least one sulfhydryl group or at least one disulfide group, and polyene compounds that have conjugated systems of double bonds; and wherein the first of said at least two compounds is lipophilic and the second of said at least two compounds is hydrophilic.

* * * * *